United States Patent
Veitinger et al.

(10) Patent No.: US 10,209,167 B2
(45) Date of Patent: Feb. 19, 2019

(54) SAMPLE PREPARATION METHOD FOR ANALYSIS OF PLATELET PROTEINS

(71) Applicant: Randox Laboratories Ltd., Antrim (GB)

(72) Inventors: Michael Veitinger, Vienna (AT); Maria Zellner, Vienna (AT)

(73) Assignee: RANDOX LABORATORIES LTD. (GB)

( * ) Notice: Subject to any disclaimer, the term of this patent is extended or adjusted under 35 U.S.C. 154(b) by 0 days.

(21) Appl. No.: 15/036,811

(22) PCT Filed: Nov. 13, 2014

(86) PCT No.: PCT/EP2014/074525
§ 371 (c)(1),
(2) Date: May 15, 2016

(87) PCT Pub. No.: WO2015/071375
PCT Pub. Date: May 21, 2015

(65) Prior Publication Data
US 2016/0266020 A1    Sep. 15, 2016

(30) Foreign Application Priority Data
Nov. 15, 2013 (GB) .................................. 1320164.5

(51) Int. Cl.
*G01N 1/40* (2006.01)
*C12Q 1/48* (2006.01)
*G01N 33/68* (2006.01)
*G01N 33/86* (2006.01)

(52) U.S. Cl.
CPC .......... *G01N 1/4077* (2013.01); *C12Q 1/485* (2013.01); *G01N 33/6842* (2013.01); *G01N 33/86* (2013.01)

(58) Field of Classification Search
CPC ......... G01N 1/4077; G01N 2015/0069; G01N 2015/0084; G01N 33/6842; G01N 33/86
See application file for complete search history.

(56) References Cited

PUBLICATIONS

Zellner, Maria et al. "Sample preparation variables in platelet proteomics for biomarker research." Chapter 3 in Platelet Proteomics, 1st Ed. John Wiley & Sons 2011. (Year: 2011).*

* cited by examiner

*Primary Examiner* — Christopher Adam Hixson
(74) *Attorney, Agent, or Firm* — Gavrilovich, Dodd & Lindsey LLP

(57) ABSTRACT

The present invention provides a novel method of in vitro sample preparation for the analysis of proteins. In a first aspect, the present invention is a method comprising the separation and individual treatment of blood platelets and platelet-poor plasma obtained from a platelet-rich plasma sample. This allows for optimal treatment of both fractions and overcomes many of the problems associated with current methods. In a second aspect of the present invention the platelet sample preparation method can be implemented before a biochip based immunoassay for the detection of platelet proteins in combination with plasma proteins.

7 Claims, 1 Drawing Sheet

---

Centrifuge 100 μl PRP for 2 min @ 3000 x g

Supernatant PPP:
• Transfer 90 μl PPP carefully into fresh tube
• Add 10 μl 10x RIPA-lysis buffer (→ 1x RIPA) and mix
• Incubate for 20 min @ 4°C

Pellet:
• Add 20 μl 5% SDS buffer to pellet and resuspend thoroughly to lyse the platelets
• Incubate for 20 min @ 4°C

• Add 70 μl 2% BSA/PBS and 10 μl 1x RIPA/PPP to pellet lysate and incubate for another 20 min @ 4°C
• Apply lysate on the biochip

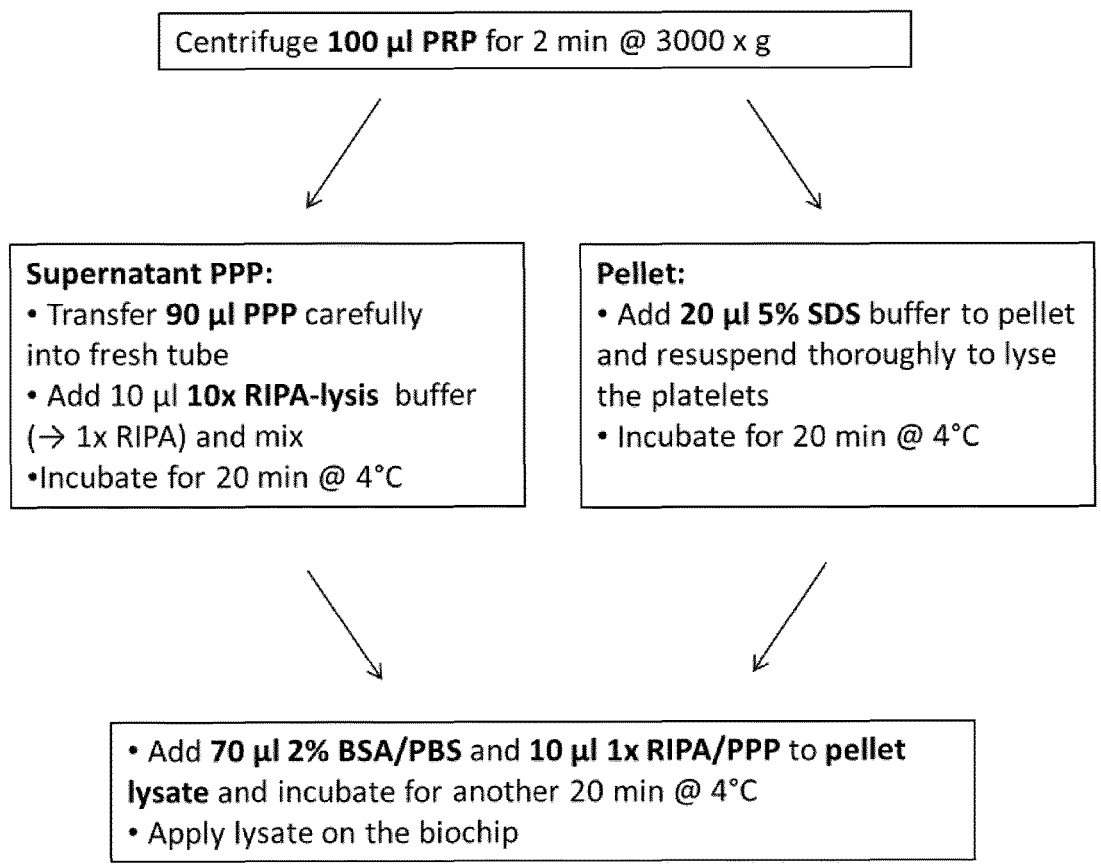

SAMPLE PREPARATION METHOD FOR ANALYSIS OF PLATELET PROTEINS

CROSS REFERENCE TO RELATED APPLICATIONS

This application is a U.S. National Stage Application filed under 35 U.S.C. § 371, and claims priority International Application No. PCT/EP2014/074525, filed Nov. 13, 2014, which application claims priority to Great Britain Application No. 1320164.5, filed Nov. 15, 2013, the disclosures of which are incorporated herein by reference in their entirety.

BACKGROUND TO THE INVENTION

The first step in the isolation of platelets for analysis is generally the separation of platelets from whole blood through centrifugation. This results in a platelet rich plasma. The abundance of plasma proteins is extremely high compared to the platelet proteome so the next phase of preparing platelets is to attempt to separate them from plasma proteins. One method commonly used to prepare a plasma-free platelet suspension involves a further centrifugation step. Under higher forces than in the initial centrifugation of the whole blood, the platelets can be pelleted and then re-suspended in a suitable buffer. The mechanical stress induced during centrifugation means that the platelets can become easily activated which results in exocytosis of secretion vesicles and granules together with a number of other biochemical changes and a change in shape. If fresh platelet samples are frozen for storage, subsequent thawing or freeze-thaw cycles can cause lysis of the platelet membranes releasing contents into the surrounding medium.

An alternative method commonly used to avoid the mechanical stress imposed by centrifugation based methods of separation is gel filtration. This consists of passing platelet-rich plasma (PRP) through a column of, for example, Sepharose 2B or Biogel A-150 which can separate platelet proteins from plasma proteins according to their size (the platelets pass through the material due to their greater mass and the plasma proteins are generally retained in the micro-pores). Compared to the centrifuged based methods separation is rapid with minimal loss of platelets from the initial PRP. However gel filtration may not eliminate all larger molecular weight plasma proteins and can be more susceptible to methodological errors (Cazenave et al, 2004).

Platelet activation/lysis is a constant problem in the preparation of platelet samples for protein analysis, as due to their highly sensitive nature they are susceptible to a number of stimuli throughout the process, from blood collection to subsequent preparation. Activation/lysis often leads to exocytosis of proteins of diagnostic interest thus potentially decreasing the value of platelets obtained. Therefore it is important to take all necessary precautions to prevent preparation induced activation/lysis while at the same time maintaining platelet yield for proteomic studies. A further problem is often encountered when an immunoassay is employed to detect platelet proteins after processing, detergents (for example, sodium dodecyl sulphate (SDS)) which are used to lyse the platelets can also disrupt epitopes as well as denature antibodies used in detection leading to distorted results (Geumann et al, 2010). Development of a platelet preparation method which addresses these problems would be extremely beneficial in the field of platelet protein immunoassays.

REFERENCES

Bertoluzzo, S. M., et al, (1999) *Blood Cell, Mol. Dis.* 25(22):339-349.

Cazenave, J-P., et al, (2004) in Methods in Molecular Biology vol 272: Platelets and Megakaryocytes Volume 1: Functional Assays. (eds) Gibbins, J. M and Mahaut-Smith, M. P. Humana Press Inc., Totowa, N.J.

Geumann, C., et al, (2010) *Analytical Biochemistry,* 402: 161-169.

Von Eggeling, F., et al, (2001) *Int. J. Mol Med.* 8(4):373-7.

SUMMARY OF THE INVENTION

The present invention provides a novel method of sample preparation for the analysis of platelet proteins. Thus, in a first aspect, the present invention is a method comprising the separation and individual treatment of blood platelets and platelet-poor plasma obtained from a platelet rich plasma sample. This allows for optimal treatment of both fractions and overcomes many of the problems associated with current methods. In a second aspect of the present invention the platelet sample preparation method can be implemented before a biochip based immunoassay for the detection of platelet proteins in combination with the desired plasma proteins.

DESCRIPTION OF THE DRAWINGS

The Invention is described with reference to the following drawing, wherein:

FIG. 1 illustrates a flow-chart summarizing the method for treatment of platelet rich plasma prior to the biochip based immunoassay.

DETAILED DESCRIPTION OF THE INVENTION

Unless otherwise stated, technical terms as used herein are used in accordance with their conventional usage as known to those skilled in the art.

The current invention provides a method of preparing a platelet sample comprising the following steps: Centrifuging a platelet suspension and separating the resultant supernatant from the pelleted platelets; separately treating this supernatant and pelleted platelets with a lysis buffer or detergent; combining these resulting lysates before analysis of platelet protein content along with desired plasma proteins.

The platelet suspension of the current invention is any medium, natural or artificial, containing platelets. Preferably the platelet suspension is a platelet-rich plasma (PRP) sample prepared from whole blood. The term 'Platelet-rich plasma' as used herein is well known in the art and generally refers to any plasma sample derived from an individual in which the platelet concentrations are above baseline blood values. PRP may be prepared from whole blood by methods commonly known in the art, for example centrifugation or sedimentation based methods. Preferably, after collection, the blood is mixed with anti-coagulant and stored at room temperature (25° C.). In the embodiment where sedimentation is used to separate the blood fractions it is preferred that, prior to sedimentation, the whole blood sample is diluted with an isotonic buffer, which may contain additives to achieve an appropriate density of plasma. For example (anti-coagulated) blood can be mixed with phosphate buffered saline (PBS) prior to sedimentation. Alternatively, (anti-coagulated) blood can be mixed directly with Dextran 500 (in PBS, e.g. 1.25% Dextran) to a final concentration of between 0.1% and 5%. Using sedimentation to separate biological samples is well known in the art and any suitable sedimentation method may be used. In a preferred embodiment of the current invention, the technique of dextran sedimentation is used, wherein the whole blood sample is applied to a solution containing dextran at a density suitable for separating platelets and plasma from other blood components (see, for example, Bertoluzzo et al, 1999). When left untouched, the plasma and platelets will separate from the other blood components, forming a yellowish supernatant. Another preferred method of separating PRP from other blood components is centrifugation. In a preferred embodiment mild centrifugation is used. Mild centrifugation refers to centrifugation forces that cause minimum or no activation of platelets. In a further preferred embodiment, mild centrifugation involves forces of 500 g or less, more preferably 250 g or less, even more preferably the mild centrifugation refers to forces of between 80-120 g.

Sedimentation or mild centrifugation of a whole blood sample results in a supernatant containing platelets and plasma, the PRP. The PRP may be used immediately, in which case an inhibitor such as prostacyclin may be used to prevent activation, or can be frozen and stored at −80° C. for later use. In the preferred method of the current invention this PRP is separated from the haematocrit then subjected to strong centrifugal forces suitable to pellet the platelets for separation from the plasma. As used herein the term 'strong centrifugal force' refers to centrifugation at 1000 g or greater, for example 1500 g, 2000 g, 2500 g or 3000 g. The centrifugation of the PRP results in pelleted platelets and a supernatant of platelet-poor plasma (PPP). The current inventors have found that this separation and individual treatment of blood platelets and PPP obtained from PRP allows for optimal treatment of both fractions.

The pelleted platelets can be treated with a lysis buffer of choice according to the proteins of interest and the desired protein conformation (reduced/non-reduced), dependent on the epitopes (continuous/discontinuous) to be recognized in subsequent steps. In a preferred embodiment of the current invention the lysis buffer used for the pelleted platelet fraction is sodium dodecyl sulphate (SDS), also known as sodium lauryl sulphate. Preferably the concentration of SDS used is 1-10%, more preferably 4-6% and in the most preferred embodiment 5%. In the present invention 5% SDS yielded the highest concentrations of both cystolic and membrane proteins from the pelleted platelets. In particular it has been found to extract membrane based proteins, such as monoamine oxidase B (Mao-B), much more efficiently than other detergents. The skilled person will understand that a variety of other detergents/reagents could be used to lyse the pelleted platelets, for example (but not limited to) Triton, CHAPS, ASB14, urea/thiourea, Nonidet P40 or C8POE.

Traditionally the supernatant PPP would be discarded, however, since this potentially contains microparticles shed from activated platelets and leaked proteins from lysed platelets, any of these proteins would be missed in subsequent analysis steps. The present invention has found a solution to the problem of missing these microparticle-trapped and lysed proteins. By also treating the PPP fraction and then pooling both treated fractions, plasmatic and cellular proteins can be analyzed in a single sample. The lysis buffer for the PPP fraction can be any suitable buffer containing ionic, non-ionic or zwitterionic detergents as chosen by the user's needs. In a preferred embodiment of the present invention, the lysis buffer for treatment of the PPP fraction is Radioimmunoprecipitation assay buffer (RIPA). RIPA buffers are well known in the art and can either be purchased commercially (e.g. Sigma) or prepared following a standard protocol. Generally a RIPA buffer comprises Tris or sodium phosphate, NaCl, SDS, sodium deoxycholate, Triton or NP-40 and also protease inhibitors such as phenylmethanesulfonyl fluoride (PMSF) and ethylenediaminetetraacetic acid (EDTA).

In a preferred embodiment of the current invention, after addition of the lysis buffers both fractions (the pelleted platelets and PPP) are incubated in accordance with the manufacturer's instructions for the chosen lysis buffer. For example incubation of the supernatant PPP with RIPA buffer is preferably at 2-8° C. for at least 5 minutes, more preferably 10 minutes, even more preferably 15 minutes and even more preferably around 20 minutes. Most preferably, in the present invention, the supernatant PPP is incubated at 4° C. for around 20 minutes. Incubation conditions for the pellet with SDS are similar, most preferably the pellet is incubated in SDS at 4° C. for around 20 minutes.

A key step in the current invention is the pooling of the two separately treated sample fractions, the pelleted platelets and the PPP, prior to analysis of their protein content. When the subsequent analysis involves protein specific antibodies a buffer, such as BSA buffer, can be added to the pelleted platelet/SDS fraction to bind excess SDS and avoid subsequent damaging of capture antibodies which may adversely affect the analysis. 70 ul of a 2% BSA buffer was added to bind excessive SDS and avoid subsequent damaging of capture antibodies. The volume of PPP added at this stage is dependent on the plasmatic protein(s) of interest. This is an advantage over current methods as most plasma proteins are highly abundant in comparison to platelet proteins and this allows for the introduction of a dilution factor. Therefore the invention enables plasma proteins to be analyzed alongside platelet proteins in a multiplex format.

Methods of measuring the level of expression of a protein from a biological sample are well known in the art and any suitable method may be used.

The level of a specific protein (or proteins) in a sample may be detected directly using a number of techniques that will be apparent to those skilled in the art. Suitable techniques typically involve contacting the sample potentially containing the protein of interest with a probe molecule that binds specifically to said protein. A subsequent wash step can remove unbound molecules and the amount of bound probe molecules is then detected, thereby determining the amount of target molecules in the sample. Preferably, to aid the detection, the probe is labelled.

For analysis of a relatively small number of proteins, a quantitative immunoassay such as a Western blot or ELISA can be used to detect the amount of protein (and therefore level of expression) in a sample.

To analyse a larger number of samples simultaneously, a protein array may be used. Protein arrays are well known in the art and function in a similar way to nucleic acid arrays, primarily using known immobilised proteins (probes) or magnetic beads to 'capture' a protein of interest. When the protein is an enzyme, an enzyme assay can be used to analyse the amount of enzyme present in a sample. A protein array contains a plurality of immobilised probes proteins. Preferably, the array contains probe proteins with affinity for different target proteins, allowing a number of different proteins to be analysed on the same support surface, preferably simultaneously. In a preferred embodiment the protein probes of the current invention are antibodies.

The advantages of this multiplexing approach are low sample volume, faster analysis of multiple samples and the ability to detect multiple markers simultaneously, which allows for combinations of markers to be assayed thereby increasing diagnostic accuracy. A support material suitable for use in a protein array is disclosed in granted European patent EP0874242. In a preferred embodiment the protein array according to the invention is analysed using the Randox Evidence System (Randox Laboratories limited, Crumlin, Northern Ireland). Alternatively, 2D Gel Electrophoresis can be used to analyse simultaneously the expression level of a number of proteins. This method is well known in the art; a sample containing a large number of proteins is typically separated in a first dimension by isoelectric focusing and in a second dimension by size. Each protein resides at a unique location (a 'spot') on the resulting gel and the amount of protein in each spot (and therefore level of expression) can be determined using a number of techniques. Difference Gel Electrophoresis (DIGE) may also be used to quantify protein expression levels (see Von Eggeling et al; Int. J. Mol Med. 2001 Oct; 8(4):373-7).

The present invention is further described with reference to the following non-limiting examples:

EXAMPLES

Example 1

Sample Preparation for Protein Biochip Analysis

Whole blood was collected in Vacuette blood tubes containing sodium citrate (Greiner Bio-One) and centrifuged for 20 min at 85-120×g, without brake (Beckman Coulter, Allegra X-12R); the upper ⅔ of the PRP fraction was carefully removed. The remaining third may contain lymphocytes and erythrocytes. The PRP was then centrifuged for 3 min at 3000×g to separate the platelets from the supernatant platelet poor plasma (PPP). Ninety µl of PPP were transferred into a fresh tube, mixed with 10 µl of 10× RIPA (1% SDS, 2.5% Na-deoxycholate, 10% Nonidet P 40, 10 mM EDTA pH 8.0, protease-phosphatase inhibitor cocktail in 1xPBS) buffer and incubated for 25 min at 4° C. In parallel, the pelleted platelets were thoroughly resuspended in 20 µl 5% SDS buffer and similarly incubated. Thereafter, the 20 µl of platelet lysate was pooled with 10 µl of the RIPA-PPP fraction, filled up with 70 µl 2% BSA/PBS buffer to a total of 100 µl and again incubated for 25 min at 4° C. before application on the protein biochip.

Example 2

Fractionated Lysis Yields a Higher Target Protein Concentration

Samples T_228 and T_147 were prepared as in example 1 however RIPA buffer was used for lysis of total PRP and PPP while urea was used for platelet lysis and analysed on the biochip for mitogen-activated protein kinase 1 (MAPK1, also known as ERK2) content (table 1).

TABLE 1

MAPK1 levels from direct PRP lysis compared to the fractionated lysis method for two samples

| Sample | Total protein concentration (ng/ml) |
|---|---|
| T_228-PRP | 223.7 |
| T_228-PPP (RIPA) + pellet (urea) | 291.1 |
| T_147-PRP | 127.1 |
| T_147-PPP (RIPA) + pellet (urea) | 136.8 |

Example 3

Comparison of Sample Lysis Methods

The sample fractionation lysis method was compared to direct lysis of the PRP and also lysis of the pelleted fraction without the addition of PPP.

PRP lysis—20 µl of 5% SDS was added to PRP samples and they were incubated at 4° C. for 30 minutes. 100 µl of each sample was applied to the biochip.

Fractionation lysis—100 µl of PRP was centrifuged for 3 min at 3000 g. 90 µl of PPP supernatant was removed to a separate eppendorf tube. 20 µl of 5% SDS was added to the remaining pellet and 10 µl of 10× RIPA was added to the PPP. Both fractions were incubated at 4° C. for 30 minutes. 10 µl of lysed PPP was added to the pellet fraction along with 80 µl of 2% BSA. 100 µl of each sample was applied to the biochip.

Pellet lysis—100 µl of PRP was centrifuged for 3 min at 3000 g in an eppendorf microcentrifuge. 90 µl of PPP was removed and discarded. 20 µl of 5% SDS was added to the pellet and incubated at 4° C. for 30 minutes. 90 µl of EV825 calibrator was added. This generic calibrator is a Tris-buffered saline with Tween-20 (TBS-T) based buffer including 6% BSA and antimicrobials (amphotericin, gentamycin sulphate and amikacin). 100 µl of each sample was applied to the biochip.

Assay diluent (200 µL) followed by calibrator/sample (100 µL) was added to the appropriate biochips. The biochips were then incubated for 60 minutes at 37° C. on a thermoshaker set at 370 rpm. The biochips were then subjected to 2 quick wash cycles using the wash buffer provided, followed by four 2 minute wash cycles. Multi-conjugate (300 µL) was added to the appropriate biochips. The biochips were then incubated for 60 minutes at 37° C. on a thermoshaker set at 370 rpm. The biochips were then subjected to 2 quick wash cycles using the wash buffer provided, followed by four 2 minute wash cycles. 250 µL of signal (1:1 luminol EV840+ peroxide, v/v) was then added to each biochip, and after 2 minutes the biochip carrier was imaged in the Evidence Investigator analyser (Randox Laboratories Ltd, Crumlin, N. Ireland).

Output from the biochip was measured in relative light units (RLUs). RLUs are arbitrary units used to quantify the signal output from the chemiluminescent reaction on the biochip and are proportional to the amount of analyte in the sample.

Tables 2 and 3 show that for both glutathione S-transferase omega 1 (GSTO1) and monoamine oxidase B (MAO-B) the fractionation approach of separately treating, and subsequently pooling, the PPP and pellet fractions following centrifugation of PRP gave higher analyte concentrations than when the sample analysed was PRP which had been directly treated or was the pellet fraction following centrifugation of PRP but without addition of PPP.

GSTO1

TABLE 2

Results expressed in relative light units (RLUs) for the detection of GSTO1 in five samples (S1-S5) using the three different sample lysis methods

| Sample | PRP | Fractionation (Pellet + PPP) | Pellet |
|---|---|---|---|
| S1 | 25684 | 36253 | 24793 |
| S2 | 10577 | 26041 | 17814 |

TABLE 2-continued

Results expressed in relative light units (RLUs) for the detection of GSTO1 in five samples (S1-S5) using the three different sample lysis methods

| Sample | PRP | Fractionation (Pellet + PPP) | Pellet |
|---|---|---|---|
| S3 | 1506 | 2182 | 131 |
| S4 | 23687 | 46308 | 41226 |
| S5 | 14166 | 34806 | 22999 |

MAO-B

TABLE 3

Results expressed in relative light units (RLUs) for the detection of MAO-B in five samples (S1-S5) using the three different sample lysis methods.

| Sample | PRP | Fractionation (Pellet + PPP) | Pellet |
|---|---|---|---|
| S1 | 1504 | 2748 | 2639 |
| S2 | 1563 | 2789 | 2292 |
| S3 | 1510 | 2750 | 2748 |
| S4 | * | 3205 | 2939 |
| S5 | * | 2282 | 2453 |

* = not detected

We claim:

1. A method of preparing an in vitro sample for protein analysis comprising the following steps:
    (i) Centrifuging a platelet suspension and separating the resultant supernatant and pelleted platelets;
    (ii) Separately treating the supernatant and pelleted platelets from step (i) with a lysis buffer or detergent; and
    (iii) Combining the resulting lysates of step (ii)
    wherein the platelet suspension is platelet-rich plasma.

2. The method of claim 1 wherein the supernatant is platelet-poor plasma.

3. The method of claim 1 wherein steps (ii) and (iii) include an incubation step, after the addition of lysis buffer or detergent in step (ii) and after combination of the lysates in step (iii).

4. The method of claim 1, wherein the lysis buffer or detergent of step (ii) used to treat the pellet fraction is Sodium dodecyl sulphate buffer.

5. The method of claim 1, wherein the protein analysis consists of an Immunoassay, protein array or 2D gel electrophoresis.

6. The method of claim 5 wherein said immunoassay is a biochip based immunoassay.

7. The method of claim 1, wherein the lysis buffer is a radioimmunoprecipitation assay buffer (RIPA).

* * * * *